US012710049B2

(12) United States Patent
Steinert et al.

(10) Patent No.: US 12,710,049 B2
(45) Date of Patent: Aug. 18, 2026

(54) PUMP UNIT FOR A CENTRIFUGAL PUMP AND A CENTRIFUGAL PUMP

(71) Applicant: Levitronix GmbH, Zürich (CH)

(72) Inventors: Daniel Steinert, Bülach (CH); Rennan Hu, Zürich (CH); Alexander Schmid, Hausen am Albis (CH); Natale Barletta, Zürich (CH)

(73) Assignee: Levitronix GmbH, Zürich (CH)

( * ) Notice: Subject to any disclaimer, the term of this patent is extended or adjusted under 35 U.S.C. 154(b) by 0 days.

(21) Appl. No.: 19/095,423

(22) Filed: Mar. 31, 2025

(65) Prior Publication Data

US 2025/0334128 A1 Oct. 30, 2025

(30) Foreign Application Priority Data

Apr. 30, 2024 (EP) .................................... 24173502

(51) Int. Cl.
*F04D 29/048* (2006.01)
*A61M 60/148* (2021.01)
(Continued)

(52) U.S. Cl.
CPC ......... *F04D 29/048* (2013.01); *A61M 60/148* (2021.01); *A61M 60/232* (2021.01);
(Continued)

(58) Field of Classification Search
CPC .............. A61M 60/422; A61M 60/232; A61M 60/148; A61M 60/419; A61M 60/822;
(Continued)

(56) References Cited

U.S. PATENT DOCUMENTS

| | | | | |
|---|---|---|---|---|
| 5,947,703 A | 9/1999 | Nojiri et al. | | |
| 6,171,078 B1 * | 1/2001 | Schob | ................ | A61M 60/824 417/423.1 |

(Continued)

FOREIGN PATENT DOCUMENTS

| | | |
|---|---|---|
| EP | 2273124 A1 | 1/2011 |
| EP | 3626277 A1 | 3/2020 |
| EP | 3795836 A1 | 3/2021 |

OTHER PUBLICATIONS

European Search Report received for EP Application No. 25170526.5, mailed on Sep. 18, 2025, 7 pages (with English Translation of Categories).

(Continued)

*Primary Examiner* — Peter J Bertheaud
(74) *Attorney, Agent, or Firm* — Spencer Fane, LLP

(57) ABSTRACT

A pump unit includes a pump housing and a rotor in the pump housing. The rotor includes vanes for conveying a fluid. Each vane extends in the axial direction to an end face. The pump unit is designed for non-contact magnetic levitation of the rotor and non-contact magnetic drive of the rotor by the stator. The pump housing has a cover part and a bottom part, the bottom part having a cylindrical cup to receive the rotor, and the cup can be inserted into the cup-shaped recess of the stator. The inlet has a lip which forms an axial end of the inlet, and projects into the pump chamber and, when viewed in the flow direction, ends in front of the end face of the rotor when the rotor is centered with respect to the axial direction in the operating state.

16 Claims, 7 Drawing Sheets

(51) Int. Cl.

| | |
|---|---|
| ***A61M 60/232*** | (2021.01) |
| ***A61M 60/419*** | (2021.01) |
| ***A61M 60/422*** | (2021.01) |
| ***A61M 60/822*** | (2021.01) |
| ***A61M 60/824*** | (2021.01) |
| ***F04D 1/00*** | (2006.01) |
| ***F04D 13/02*** | (2006.01) |
| ***F04D 13/06*** | (2006.01) |
| ***F04D 29/42*** | (2006.01) |
| ***F04D 29/62*** | (2006.01) |

(52) U.S. Cl.
CPC ........ *A61M 60/419* (2021.01); *A61M 60/422* (2021.01); *A61M 60/822* (2021.01); *A61M 60/824* (2021.01); *F04D 13/024* (2013.01); *F04D 13/026* (2013.01); *F04D 13/027* (2013.01); *F04D 13/06* (2013.01); *F04D 13/064* (2013.01); *F04D 13/0666* (2013.01); *F04D 29/42* (2013.01); *F04D 29/426* (2013.01); *F04D 29/4273* (2013.01); *F04D 29/628* (2013.01); *F04D 1/00* (2013.01)

(58) Field of Classification Search
CPC .. A61M 60/824; F04D 29/048; F04D 13/064; F04D 13/0666; F04D 13/026; F04D 13/027; F04D 13/06; F04D 29/426; F04D 13/024; F04D 29/628; F04D 29/42; F04D 29/4273
See application file for complete search history.

(56) References Cited

U.S. PATENT DOCUMENTS

| | | | | |
|---|---|---|---|---|
| 2019/0013747 | A1* | 1/2019 | Barletta ................. | H02K 1/276 |
| 2019/0167876 | A1 | 6/2019 | Yanai et al. | |
| 2021/0079922 | A1 | 3/2021 | Schmid et al. | |

OTHER PUBLICATIONS

European Search Report corresponding to application No. 24173502.6-1004 dated Oct. 28, 2024. English translation of categories attached.

* cited by examiner

A
1'
21'
22'
4'
2'
103'
23'
103'
3'
101'
31'
10'

D2
A;M
1
28
21
2
22
221
107
23
4
103
T
DL
109
108
24
103
25
31
101
102
8
104
10
3
D1

D2
A;M
21
1
22
28
8
2
T
23
103
10
25
101
D1

A;M
8
1
21
22
28
2
23
103
10
25
101

A;M
28
21
1
22
4
2
221
23
103
10
25
104
101

A;M
21
α
4
2
1
22
28
221
23
108
103
109
10
25
104
101

PUMP UNIT FOR A CENTRIFUGAL PUMP AND A CENTRIFUGAL PUMP

CROSS REFERENCE TO RELATED APPLICATIONS

This application claims priority to European Application No. EP 24173502.6, filed Apr. 30, 2024, the contents of which are hereby incorporated by reference.

BACKGROUND

Technical Information

The disclosure relates to a pump unit for a centrifugal pump. The disclosure further relates to a centrifugal pump with such a pump unit.

Background Information

Centrifugal pumps are known which comprise a pump unit and a stator which is designed as a drive unit for the rotor of the pump unit, wherein the rotor of the pump unit forms the centrifugal wheel of the centrifugal pump. The rotor can be magnetically supported without contact and can be driven without contact to rotate about an axial direction by the stator in the pump unit. Such centrifugal pumps are known, for example, under the product name Levitronix® BPS pumps.

The stator and the rotor form an electromagnetic rotary drive. In the Levitronix® BPS pumps, for example, the electromagnetic rotary drive is designed according to the principle of the bearingless motor. The term bearingless motor refers to an electromagnetic rotary drive in which the rotor can be supported completely magnetically with respect to the stator, wherein no separate magnetic bearings are provided. For this purpose, the stator is designed as a bearing and drive stator, which is both the stator of the electric drive and the stator of the magnetic bearing. A magnetic rotating field can be generated with the electrical windings of the stator, which on the one hand exerts a torque on the rotor, which effects its rotation about a desired axis of rotation defined by the axial direction and which, on the other hand, exerts an arbitrarily adjustable transverse force on the rotor so that its radial position can be actively controlled or regulated. Thus, three degrees of freedom of the rotor can be actively regulated, namely its rotation and its radial position (two degrees of freedom). With respect to three further degrees of freedom, namely its position in axial direction and tilting with respect to the radial plane perpendicular to the desired axis of rotation (two degrees of freedom), the rotor is passively magnetically supported or stabilized by reluctance forces, i.e., it cannot be controlled. The absence of a separate magnetic bearing with a complete magnetic bearing of the rotor is the property, which gives the bearingless motor its name. In the bearing and drive stator, the bearing function cannot be separated from the drive function.

Of course, other designs of centrifugal pumps are also known in which the rotor is magnetically supported without contact, for example those in which separate magnetic bearings are provided for the rotor so that the magnetic bearing function is separated from the drive function. For example, separate coils are provided for this purpose, with which only the bearing forces for the rotor are realized, but which do not contribute to the drive of the rotor. For example, such a centrifugal pump is disclosed in WO 2022/004144.

Centrifugal pumps with non-contact magnetically supported and driven rotors, for example those which are designed and operated according to the principle of the bearingless motor, have proven themselves in a large number of applications. Due to the absence of mechanical bearings, such centrifugal pumps are suitable for applications in which very sensitive substances are conveyed, for example blood pumps, or on which very high demands are made with respect to purity, for example in the semiconductor industry, the pharmaceutical industry, the biotechnological industry, or with which abrasive or aggressive substances are conveyed, which would very quickly destroy mechanical bearings, for example pumps for slurry, sulfuric acid, phosphoric acid or other chemicals in the semiconductor industry.

FIG. 1 shows a representation of a centrifugal pump known from the state of the art, which is designed according to the principle of the bearingless motor. This is a Levitronix® BPS pump, for example. For better understanding, a segment has been cut out in FIG. 1 so that the inside of the centrifugal pump is visible.

The centrifugal pump 200' comprises a stator 100' and a pump unit 1'. For better understanding, FIG. 2 shows a top view of the pump unit 1' from the axial direction A and FIG. 3 shows the pump unit 1' in a sectional view along the sectional line III-III in FIG. 2.

To indicate that the representation in FIG. 1, FIG. 2 and FIG. 3 is a device from the state of the art, the reference signs are each marked here with an inverted comma or with a dash. The centrifugal pump is designated in its entirety by the reference sign 200'.

A rotor 10' is arranged in the pump unit 1', which forms the centrifugal wheel or the impeller with which the fluid is conveyed. The stator 100' has a stator housing 130' and extends in an axial direction A from a first axial end 110' to a second axial end 120', wherein a cup-shaped recess 121' is provided at the first axial end 110', into which recess the pump unit 1' can be inserted. The stator 100' together with the rotor 10' forms an electromagnetic rotary drive for rotating the rotor 10' about the axial direction A. The stator 100' is designed for non-contact magnetic bearing of the rotor 10' according to the principle of the bearingless motor. For this purpose, the stator 100' is designed as a bearing and drive stator, with which the rotor 10' can be magnetically driven without contact for rotation about the axial direction A and can be magnetically supported without contact with respect to the stator 100', wherein the rotor 10' is passively magnetically stabilized with respect to the axial direction A and is actively magnetically supported in a radial plane perpendicular to the axial direction A, which is indicated by the line E in FIG. 1.

The electromagnetic rotary drive with the stator 100' and the rotor 10' is designed as a so-called temple motor. The stator 100' comprises a plurality of coil cores 125', here eight coil cores 125', each of which comprises a longitudinal leg 126', which extends from a first end, in FIG. 1 the lower end according to the representation, in the axial direction A to a second end, and a transverse leg 127', which is arranged at the second end of the longitudinal leg 126' and in the radial plane E. Each transverse leg 127' extends from the associated longitudinal leg 126' in radial direction towards the rotor 10' and is delimited by a radially inside located end surface. The coil cores 126' are arranged around the cup-shaped recess 121' with respect to the circumferential direction and thus around the rotor 10', so that the rotor 10' is arranged between the radially inside located end surfaces of the transverse legs 127' of the coil cores 126'.

All first ends of the longitudinal legs 126' are connected to one another by a back iron 122' for conducting the magnetic flux. At least one concentrated winding 160', 161' is provided at each longitudinal leg 126', which surrounds the respective longitudinal leg 126'. With respect to the number and arrangement of the concentrated windings 160', 161', many variants are known, which are not explained in more detail here. For example, there are such windings 160' which are wound around exactly one longitudinal leg 126' and such windings 161' which are arranged around exactly two longitudinal legs 126'.

The plurality of the longitudinal legs 126', which extend in the axial direction A and are reminiscent of the columns of a temple has given the temple motor its name.

The pump unit 1' (FIG. 2, FIG. 3) comprises a pump housing 2' with an inlet 21' and with an outlet 22' for the fluid to be conveyed, as well as the rotor 10' arranged in the pump housing 2' for conveying the fluid, which rotor can be rotated about the axial direction A. The pump housing 2' delimits a pump chamber 23'. The rotor 10' comprises a magnetically effective core 101', which cooperates magnetically with the stator 100' to generate the torque as well as to generate the magnetic bearing forces. For example, the magnetically effective core 101' is a permanent magnetic ring or a permanent magnetic disk.

In the operating state, it is the desired position of the rotor 10' that the rotor 10' is centered with respect to the axial direction A and is centered in the radial plane E between the coil cores 125', here the transverse legs 127' of the coil cores 125'. Centered with respect to the axial direction A means that the magnetically effective core 101' of the rotor is aligned with the transverse legs 127' of the coil cores 125'. The magnetic center plane of the rotor 10'-usually this is the geometric center plane of the magnetically effective core 101'-then lies in the radial plane E. If the rotor 10' is deflected out of this centered desired position in the axial direction or tilted against the axial direction A, this results in magnetic restoring forces which move the rotor 10' back to its desired position.

Such designs are also possible in which the magnetically effective core 101' is designed in a permanent magnetic-free manner, i.e., without permanent magnets. The rotor 10' is then designed as a reluctance rotor, for example. Then, the magnetically effective core 101' of the rotor 10' is made of a soft magnetic material, for example. Suitable soft magnetic materials for the magnetically effective core 101' are, for example, ferromagnetic or ferrimagnetic materials, i.e. in particular iron, nickel-iron, cobalt-iron, silicon-iron, mu-metal.

Furthermore, designs are possible in which the magnetically effective core 101' of the rotor 10' comprises both ferromagnetic materials and permanent magnetic materials. For example, permanent magnets can be placed or inserted into a ferromagnetic base body. Such designs are advantageous, for example, if one wishes to reduce the costs of large rotors by saving permanent magnetic material.

Typically, the magnetically effective core 101' is completely encased in a plastic. In other designs, the magnetically effective core 101' is completely enclosed in a sheath consisting of a ceramic material or a metallic material, for example a stainless steel or titanium or tantalum.

Furthermore, the rotor 10' comprises a plurality of vanes 103' for conveying the fluid from the inlet 21' to the outlet 22'.

The pump housing 2' comprises a bottom part 3' and a cover part 4' for closing the bottom part 3', wherein a sealing element 90' (FIG. 1) is provided between the bottom part 3' and the cover part 4', for example an O-ring or a flat seal, in order to prevent a leakage of the fluid into the environment.

The inlet 21' of the pump housing 2' is arranged in the cover part 4' and is designed such that the fluid to be conveyed flows towards the rotor 10' in the axial direction A. The outlet 22' extends parallel to the radial plane E, i.e. substantially perpendicular to the inlet 21'. Usually, the inlet 21' is designed in such a way that it forms a rounded transition into the pump chamber 23'.

The bottom part 3' of the pump housing 2' has a cylindrical cup 31' for receiving the rotor 10'. The cup 31' is inserted into the recess 121' in the stator housing 130' so that the rotor 10', more precisely the magnetically effective core 101' of the rotor 10', is arranged between the transverse legs 127' of the coil cores 126'.

For example, the pump unit 1' is attached to the stator housing 130' by attachment elements 11', e.g. a plurality of screws 11'. The screws 11' are arranged at the bottom part 3' and fix the bottom part 3' to the first axial end 110' of the stator 100'. Usually, the cover part 4' is connected to the bottom part 3' via a press fit. In addition, the cover part 4' is fixed to the bottom part 3' by several attachment screws 13', which engage through the cover part 4' in axial direction A and engage in the bottom part 3'.

For many applications, for example for applications in the semiconductor industry, the pump unit 1'—with the exception of the magnetically effective core 101'—is made of a plastic, for example of a perfluoroalkoxy polymer (PFA) or of polytetrafluoroethylene (PTFE), because these are plastics with a particularly high chemical resistance. These plastics are practically inert materials that cannot be attacked even by chemically very aggressive substances, such as those frequently used in the semiconductor industry. In addition, PFA and PTFE are very pure plastics because they usually have no additives, and their molecular complexes are at least approximately inert. PFA is often preferred because it can be processed in injection molding processes.

SUMMARY

Even though this type of pump units 1' and centrifugal pumps 200' has proven very successful in practice, it has been determined that there is still room for improvement, in particular when these centrifugal pumps 200' are designed for very high outputs. Particularly at high hydraulic outputs, a high leakage flow occurs, which is directed from the trailing edges of the vanes 103' in the direction of the inlet 21'. The leakage flow is indicated in FIG. 3 by the arrows without reference signs. This leakage flow reduces the efficiency of the centrifugal pump and thus, of course, also its energy efficiency. In addition, the leakage flow causes tear-off effects, in particular in the area of the inlet, which can lead to cavitation and to a further reduction in efficiency.

Starting from this state of the art, it is therefore an object of the disclosure to propose a pump unit with a rotor for a centrifugal pump that can be magnetically levitated without contact, which pump unit, in particular, but not only, enables a very high efficiency of the centrifugal pump at high hydraulic outputs. In addition, it is an object of the disclosure to propose a centrifugal pump with such a pump unit.

The subject matter of the disclosure meeting this object is characterized by the features disclosed herein.

According to the disclosure, a pump unit for a centrifugal pump is thus proposed, which comprises the pump unit and a stator extending in an axial direction from a first axial end to a second axial end, wherein a cup-shaped recess is provided at the first axial end, into which the pump unit can be inserted, wherein the pump unit has a pump housing with an inlet and with an outlet for a fluid to be conveyed as well as a rotor arranged in the pump housing with a plurality of vanes for conveying the fluid, wherein each vane extends in the axial direction to an end face of the rotor facing the inlet, wherein the pump housing delimits a pump chamber, wherein the rotor can be rotated about the axial direction, wherein the pump unit is designed for a non-contact magnetic levitation of the rotor and for a non-contact magnetic drive of the rotor by the stator, wherein the pump housing has a cover part and a bottom part, wherein the bottom part has a cylindrical cup for receiving the rotor, which cup can be inserted into the cup-shaped recess of the stator. The inlet has a lip which forms one axial end of the inlet, wherein the lip projects into the pump chamber and, when viewed in the flow direction, ends in front of the end face of the rotor when the rotor is centered with respect to the axial direction in the operating state.

If the rotor is thus in its desired position in the operating state, i.e. centered with respect to the axial direction, then the lip has a distance from the end face of the rotor, when viewed in the axial direction, so that the lip does not project into the rotor. Of course, due to the magnetic levitation of the rotor, it is possible that the rotor displaces in its entirety in the axial direction in the operating state. Due to such displacements of the rotor in the axial direction, it is possible in the operating state that, depending on the design of the lip, the lip immerses into the rotor with respect to the axial direction. Therefore, the statement that the lip ends in front of the end surface of the rotor with respect to the axial direction when viewed in the flow direction, refers to such an operating state in which the rotor is centered with respect to the axial direction, i.e., it is in its desired position.

The lip, which forms one axial end of the inlet and projects into the pump chamber, significantly reduces the leakage flow that flows from the trailing edge of the vanes in the direction of the inlet 21, because the lip reduces the free flow cross-section for this leakage flow as it projects into the pump chamber. Alternatively, the lip enables a higher design of the pump chamber with respect to the axial direction, without increasing the free flow cross-section for the leakage flow. Furthermore, the lip forms a well-defined tear-off edge for the fluid flowing through the inlet. Due to this defined tear-off edge, it is determined where the flow tears off at the inlet, independently of the specific properties of the fluid, such as its viscosity, and independently of the specific flow conditions, such as the flow rate. Since the leakage flow from the trailing edge of the vanes to the inlet of the pump housing is significantly reduced, the efficiency of the centrifugal pump increases. Furthermore, tear-off effects caused by the leakage flow, which can for example cause cavitations, are at least significantly reduced.

By reducing the leakage flow, the disturbing forces acting on the rotor in the radial direction are also significantly reduced. In doing so, the electrical current required for the active magnetic radial levitation of the rotor also reduces, which increases the efficiency and energy efficiency of the centrifugal pump.

A further advantage of the lip acting as a tear-off edge is that the static and dynamic axially directed forces on the rotor are reduced because the suction effect on the cover part of the pump housing is minimized.

Since the lip of the inlet projects into the pump chamber, a valve-like effect of the inlet is also created. This is advantageous with regard to the axial stabilization of the rotor, both with regard to tilting of the rotor and axial displacement of the rotor.

Preferably, the lip is designed in a ring-shaped manner and extends along the entire circumference of the inlet with respect to the circumferential direction. However, embodiments are also possible in which the lip, when viewed in the circumferential direction, is provided with one gap or with several gaps. For example, the lip can be designed in a crenellated manner. Thus, the lip can be designed with interruptions with respect to the circumferential direction.

According to a preferred embodiment, the vanes of the rotor are arranged around a central inlet area which extends in the axial direction to the end face of the rotor, and which has a diameter. The central inlet area of the rotor is free of vanes. Each vane extends from a radially inwardly arranged leading edge to a radially outwardly arranged trailing edge. The leading edges of the vanes lie on a line, preferably a circular line, which has a distance from the center axis of the rotor that is different from zero. The diameter of the central inlet area is determined by the distance of the leading edges of the vanes from the center axis of the rotor. The diameter of the central inlet area is equal to twice the distance of the leading edges of the vanes from the center axis of the rotor.

Furthermore, it is preferred that the rotor has at least one relief opening extending from the central inlet area in the axial direction through the rotor. Due to this central relief opening, the axial thrust acting on the rotor can be reduced.

According to a preferred embodiment, the lip of the inlet has an outer diameter which is larger than the diameter of the central inlet area. However, embodiments are also possible in which the outer diameter of the lip is smaller than the inner diameter of the central inlet area. In these embodiments, it is then possible that the lip enters the central inlet area of the rotor in the operating state due to an axial displacement of the rotor.

According to a preferred embodiment, the lip has a substantially triangular profile, the apex of which faces the end face of the rotor. As a result, the end of the inlet facing the rotor is designed as a narrow edge, which is advantageous with regard to its function as a tear-off edge. It is understood that in the case of the substantially triangular profile, the apex is not designed as a sharp edge, i.e. not in the sense of a blade, but as an edge with a finite width.

Furthermore, it is a preferred measure that the lip widens when viewed in the flow direction. The cross-sectional area of the lip thus increases when viewed in the flow direction. For example, the lip can be designed to widen conically with respect to the axial direction.

Embodiments are also possible in which the lip is designed to be outwardly curved.

It is a further possible embodiment that the lip is designed as a cylindrical pipe section.

According to a further embodiment, the cover part of the pump housing is designed in an oblique manner so that the cover part encloses an angle with the axial direction at the inlet which is greater than 90°.

According to a further preferred embodiment, the outlet has an entry surface through which the fluid can flow from the pump chamber into the outlet, wherein the entry surface of the outlet has a profile which is different from a circular surface. Due to this embodiment of the entry surface of the outlet, the distance between the entry surface and the vanes measured in the axial direction can be significantly reduced without having to reduce the cross-sectional area of the entry surface. Since the profile of the entry surface of the outlet is different from a circular surface, the entry surface can be arranged closer to the vanes with respect to the axial direction than with a circular profile of the entry surface, without reducing the cross-sectional area of the entry surface.

For example, if an entry surface with a circular profile that has a determined diameter is compared with an entry surface with a non-circular profile, the entry surface with the non-circular profile can be designed with a larger cross-sectional area than the entry surface with a circular profile, without the maximum extension of the entry surface with the non-circular profile being greater than the determined diameter of the entry surface with the circular profile.

Conversely, this means that the entry surface with the non-circular profile can be designed with the same cross-sectional area but with a smaller extension, particularly in the axial direction, compared to an entry surface with a circular profile. Thus, the entry surface with the non-circular profile can be arranged closer to or with a greater overlap with the vanes with respect to the axial direction. This has a particularly advantageous effect on the non-contact magnetic levitation of the rotor, because the static and dynamic axial and tilting forces on the rotor as well as the disturbing forces acting on the rotor in the radial direction are significantly reduced.

According to a preferred embodiment, the profile of the entry surface is substantially designed in a rectangular manner.

Furthermore, it is a preferred embodiment, particularly for reasons of production technology, that the profile of the entry surface is designed with rounded corners.

According to a preferred embodiment, the profile of the entry surface has a profile height in the axial direction as well as a profile width in a radial direction perpendicular to the axial direction, wherein the profile width is greater than the profile height.

Furthermore, a centrifugal pump for conveying a fluid is proposed by the disclosure, with a pump unit designed according to the disclosure, and with a stator extending in an axial direction from a first axial end to a second axial end, wherein a cup-shaped recess is provided at the first axial end, into which the cylindrical cup of the pump unit can be inserted, wherein the stator together with the rotor forms an electromagnetic rotary drive for rotating the rotor about the axial direction, wherein the stator is designed as a bearing and drive stator with which the rotor can be magnetically driven without contact and magnetically levitated without contact with respect to the stator, wherein the rotor is passively magnetically stabilized with respect to the axial direction and is actively magnetically levitated in a radial plane perpendicular to the axial direction.

Particularly preferably, the electromagnetic rotary drive is designed as a temple motor, wherein the stator has a plurality of coil cores, each of which comprises a longitudinal leg extending from a first end in the axial direction to a second end, as well as a transverse leg which is arranged at the second end of the longitudinal leg and in the radial plane, and which extends from the longitudinal leg in the radial direction, wherein the coil cores are arranged around the rotor with respect to the circumferential direction, so that the rotor is arranged between the transverse legs of the coil cores, and wherein at least one concentrated winding is provided at each longitudinal leg, which winding surrounds the respective longitudinal leg.

Further advantageous measures and embodiments of the disclosure are apparent from the disclosure.

BRIEF DESCRIPTION OF THE DRAWINGS

In the following, the disclosure will be explained in more detail with reference to embodiments and with reference to the drawing. In the schematic drawing show (partially in section).

DETAILED DESCRIPTION

Figure 1:
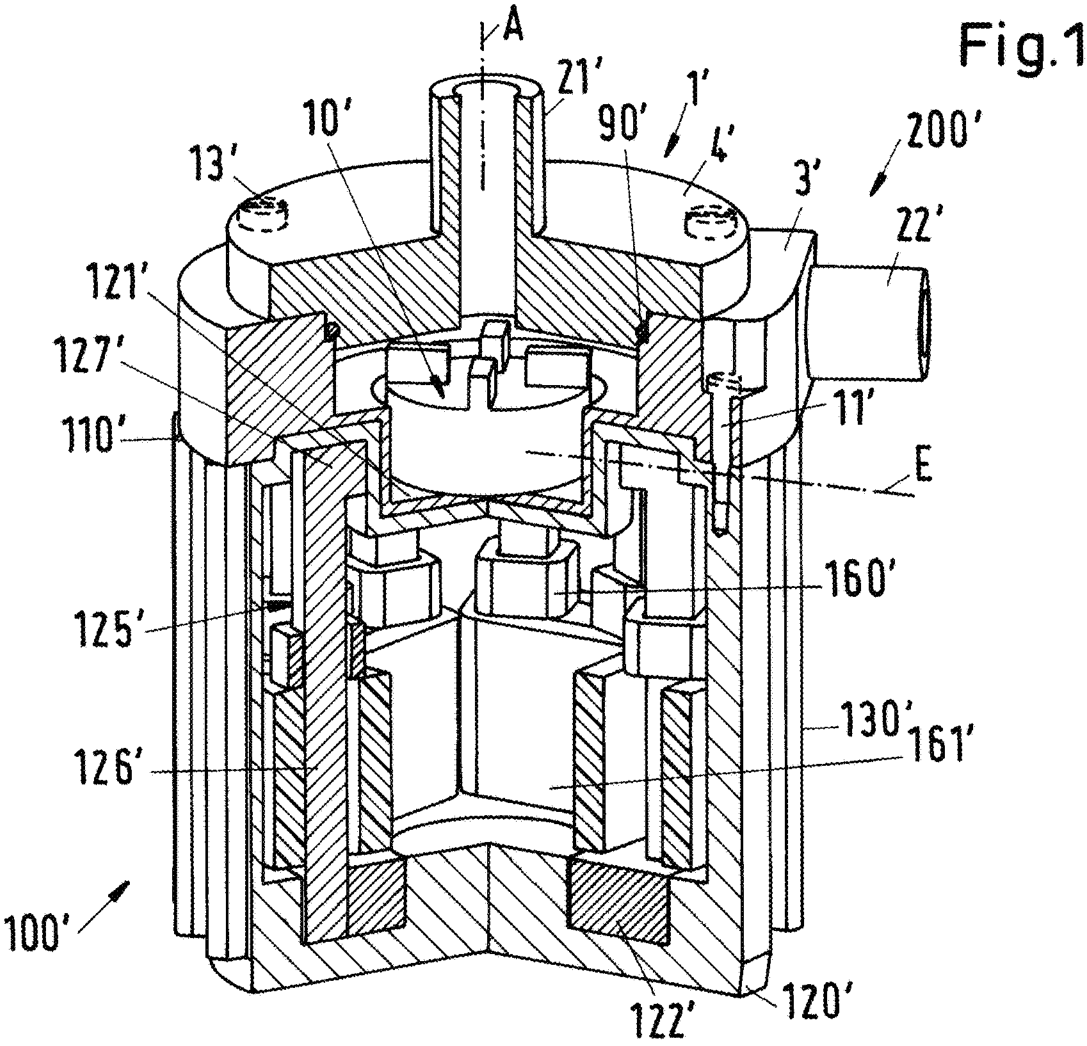
FIG. 1 is a perspective view of a centrifugal pump according to the state of the art, partly in section.
Figure 2:
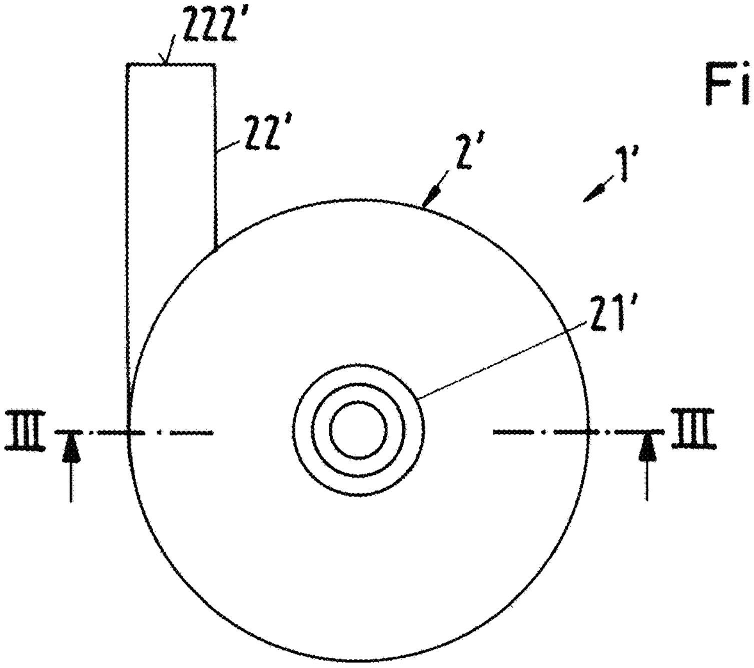
FIG. 2 is a top view of the pump unit from the axial direction A.
Figure 3:
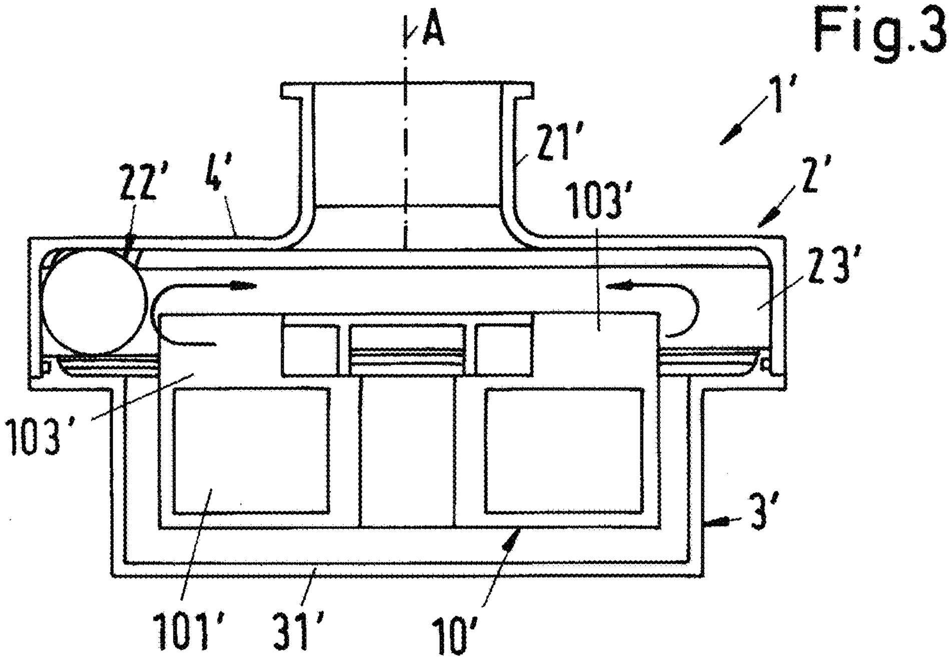
FIG. 3 is the pump unit from FIG. 2 in a sectional view along the section line III-III in FIG. 2.

As already explained above, FIG. 1 shows a centrifugal pump 200' with a non-contact magnetically supported and non-contact magnetically driven rotor 10', which is known from the state of the art. FIG. 2 and FIG. 3 show the pump unit 1' of this centrifugal pump 200' in a top view and in a sectional view, respectively.

Figure 4:
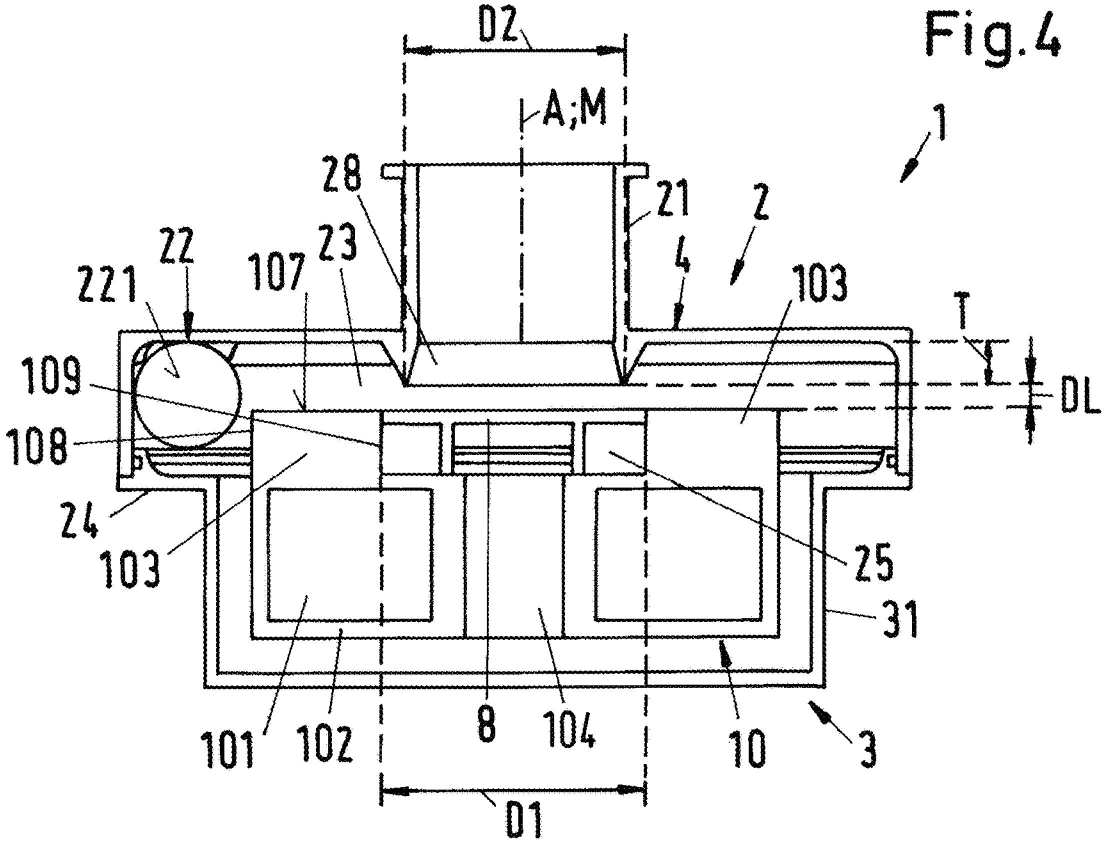
FIG. 4 is a first embodiment of a pump unit according to the disclosure in a sectional view along the axial direction.

In a sectional view corresponding to FIG. 3, FIG. 4 shows a first embodiment of a pump unit according to the disclosure, which is designated in its entirety by the reference sign 1.

The pump unit 1 is designed for a centrifugal pump 200 (see FIG. 12) for conveying a fluid and comprises a pump housing 2 with an inlet 21 and with an outlet 22 for the fluid. A rotor 10 for conveying the fluid is arranged in the pump housing 2, which rotor forms the centrifugal wheel or the impeller of the pump unit 1 and thus of the centrifugal pump 200. The rotor 10 can be rotated about a desired axis of rotation, which defines an axial direction A. This desired axis of rotation is the central axis M of the rotor 10.

With respect to the axial direction A, the rotor 10 extends from an end face 107 facing the inlet 21 to a back side facing away from the inlet 21.

A direction perpendicular to the axial direction A is designated as the radial direction. In the following, the term “axial” is used with the generally accepted meaning “in axial direction” or “with respect to the axial direction”. The term “radial” is used with the generally accepted meaning “in radial direction” or “with respect to the axial direction”.

The pump unit 1 is designed for a non-contact magnetic levitation of the rotor 10 and for a non-contact magnetic drive of the rotor 10. This can be realized in particular in the analogously same way as explained on the basis of FIG. 1 to FIG. 3. Thus, the pump unit 1 according to the disclosure can be designed in the analogously same way with respect to the magnetic levitation and the magnetic drive as the pump unit 1' in FIG. 3. For this purpose, the rotor 10 of the pump unit 1 comprises a magnetically effective core 101, which is designed, for example, as a permanent magnetic ring or permanent magnetic disk and is enclosed by a sheath 102. The sheath 102 is preferably designed as a plastic sheath. The sheath 102 is made of PTFE or PFA, for example. The magnetically effective core 101 is encapsulated in the sheath 102, i.e. the sheath 102 completely and preferably hermetically encloses the magnetically effective core 101. As a result, the magnetically effective core 101 is protected from the fluid. The sheath 102 can be produced, for example, by spraying a plastic around the magnetically effective core 101.

The magnetically effective core 101 of the rotor 10 is that component of the rotor 10, which cooperates magnetically with the stator 100 to generate the torque as well as to generate the magnetic levitation forces.

Furthermore, the rotor 10 comprises a plurality of vanes 103 for conveying the fluid from the inlet 21 to the outlet 22. The vanes 103 are arranged on the sheath 102 of the magnetically effective core 101. The vanes 103 are preferably made of plastic and can, for example, be designed in one piece with the sheath 102. Of course, it is also possible to produce the individual vanes 103 or the entirety of the vanes 103 in a separate manufacturing process and then connect them to the sheath 102 of the magnetically effective core 101, for example by a welding process.

The impeller with the vanes 103 formed by the rotor 10 is preferably designed as radial impeller, which is approached by the fluid from the inlet 21 in the axial direction A, and then redirects the fluid in a radial direction.

The pump housing 2 comprises a cover part 4 and a bottom part 3, which are connected to each other in a sealing manner, which is not represented in more detail in FIG. 4 because it is not necessary for the understanding of the disclosure. The bottom part 3 comprises a cylindrical cup 31 for receiving the rotor 10. The cup 31 is preferably designed and arranged such that it can be inserted into a cup-shaped recess of a stator 100, as is represented schematically in FIG. 12.

The stator 100 (FIG. 12) extends in the axial direction A from a first axial end 110 to a second axial end 120 and has a stator housing (not represented in FIG. 12), which is substantially designed in a cylindrical manner. The cup-shaped recess is arranged at the first axial end 110 of the stator 100, preferably centrally in the end surface which forms the first axial end 110 of the stator 100. The design of the stator housing with the cup-shaped recess can in particular be realized in a way analogous to that explained on the basis of FIG. 1 for the stator housing 130' and the cup-shaped recess 121'. Thus, the cup 31 is then arranged and designed in such a way that it can be inserted into the recess 121' (FIG. 1) in the first axial end 110' of the stator 100', and the magnetically effective core 101 is arranged between the transverse legs 127' of the coil cores 125'.

As can be recognized in FIG. 4, there is a pump chamber 23 above the cup 31 according to the representation, which is delimited by the pump housing 2 and in which the vanes 103 of the rotor 10 are arranged. The pump chamber 23 is designed at least substantially in a cylindrical manner, wherein the diameter of the pump chamber 23 is larger than the inner diameter of the cup 31. As a result, the pump housing 2 has a flange-like projection 24, which delimits the pump chamber 23 downward with respect to the axial direction A according to the representation.

The inlet 21 is centrally arranged in the cover part 3 of the pump housing 2 so that the fluid can flow towards the rotor 10 in the axial direction A.

Figure 12:
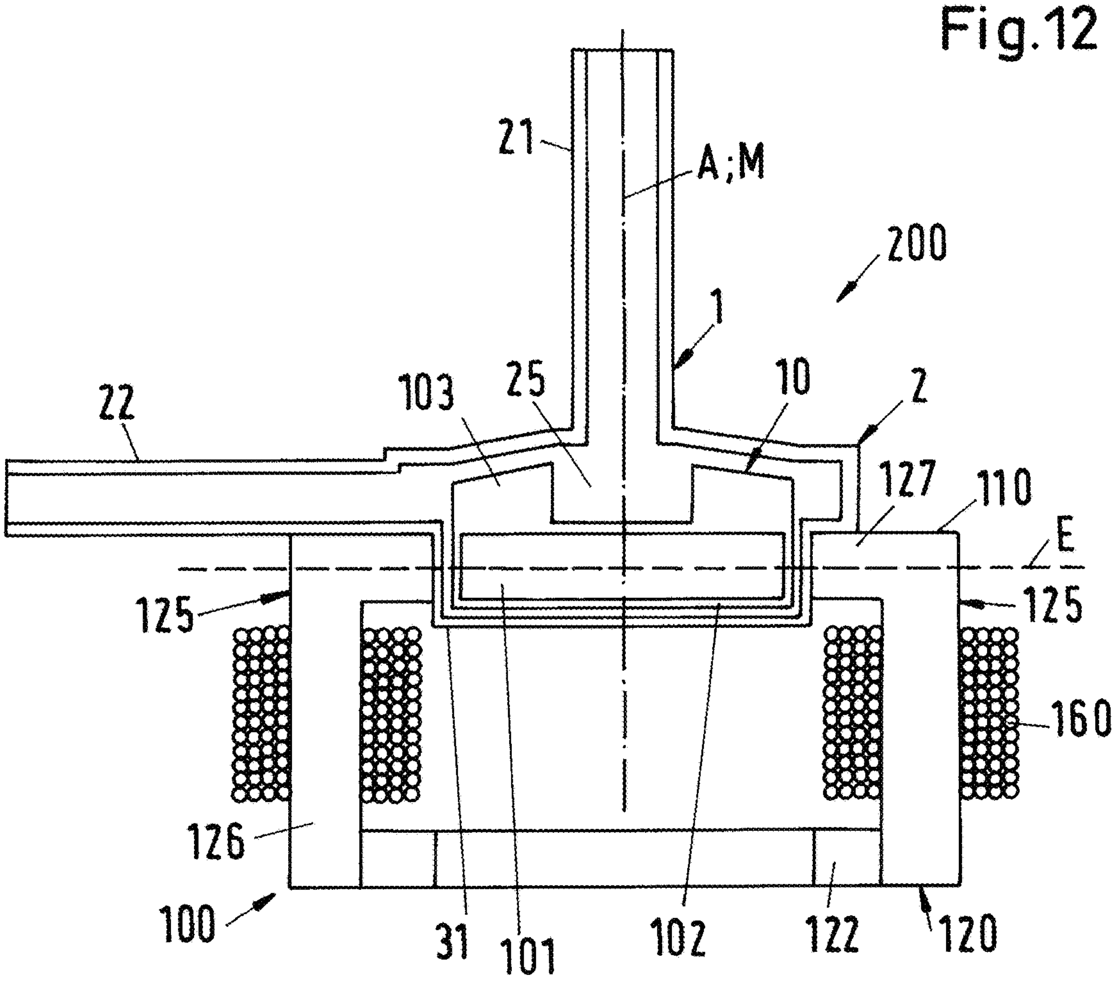
FIG. 12 is a schematic sectional view of an embodiment of a centrifugal pump according to the disclosure.

Each vane 103 extends from a radially inwardly arranged leading edge 109 to a radially outwardly arranged trailing edge 108. In the embodiment described here, the vanes 103 are designed with an exemplary character such that they extend in a straight line in the radial direction from the leading edge 109 to the trailing edge 108 and have a constant height over their entire extension. Here, the height refers to the extension of the vanes 103 in the axial direction A. As already mentioned, this design is only to be understood as an example. In other embodiments, the vanes 103 are designed, for example, in a curved manner with respect to the radial direction, and/or with a height in the axial direction A which changes from the leading edge 109 to the trailing edge 108. For example, an embodiment is shown in FIG. 12 in which the vanes 103 have a greater height at their leading edge 109 than at their trailing edge 108.

Furthermore, a ring-shaped cover plate 8 is optionally provided, which is arranged on the upper edges of the vanes 103 facing the inlet 21. The cover plate 8 covers all vanes 103. With respect to the radial direction, the ring-shaped cover plate 8 extends from the leading edges 109 of the vanes 103 to their trailing edges 108. The cover plate 8 forms the end face 107 of the rotor 10 here. If the rotor 10 is designed without the cover plate 8, the upper edges of the vanes 103 facing the inlet form the end face of the rotor 10.

The vanes 103 of the rotor 10 are arranged around a central inlet area 25 which is free of vanes 103. The leading edges 109 of the vanes 103 lie on a line, here on a circular line, which has a distance different from zero from the center axis M of the rotor 10. The diameter D1 of the central inlet area 25 is determined by the distance of the leading edges 109 of the vanes 103 from the center axis M of the rotor 10. This diameter D1 of the central inlet area 25 is equal to twice the distance of the leading edges 109 of the vanes 103 from the center axis of the rotor 10. In the embodiment described here, the diameter D1 of the central inlet area 25 is the same size as the inner diameter of the ring-shaped cover plate 8. With respect to the axial direction A, the central inlet area 25 extends along the leading edges 109 of the vanes 103 to the end face 107 of the rotor 10.

If the leading edges 109 of the vanes run not parallel to the axial direction A but are inclined with respect to the axial direction A, for example, the diameter D1 of the central inlet area 25 is determined by the distance of the leading edges 109 at the upper edges of the vanes 103 facing the inlet 21.

Furthermore, the rotor 10 comprises a relief opening 104, which is designed in a circular cylindrical manner and extends in the axial direction A. The relief opening 104 is arranged centrally in the rotor 10, such that the axis of this relief opening 104 coincides with the center axis M of the rotor 10. The relief opening 104 extends from the central inlet area 25 in the axial direction A through the rotor 10 to the back side of the rotor 10.

The outlet 22 has an entry surface 221 through which the fluid can flow out of the pump chamber 23 into the outlet 22, and an exit surface (not visible in FIG. 4) through which the fluid leaves the outlet 22. As is generally the case, the profile of the entry area 221 refers to the cross-sectional area perpendicular to the main direction of flow of the fluid in the outlet 22. As represented in FIG. 4, the profile of the entry surface 221 is a circular surface. The profile of the entry surface 221 is the perpendicular projection of the entry surface 221 onto a plane which stands perpendicular on the flow direction of the fluid in the outlet 22.

According to the disclosure, the inlet 21 comprises a lip 28, which forms one axial end of the inlet 21, wherein the lip 28 projects into the pump chamber 23 and is spaced apart from the end face 107 of the rotor 10 with respect to the axial direction A when the rotor 10 is centered with respect to the axial direction A in the operating state. When viewed in the flow direction of the fluid, the lip 28 ends in front of the end face 107 of the rotor 10. The lip 28 is preferably designed in a ring-shaped manner.

Due to the magnetic levitation of the rotor 10, it is of course possible in the operating state that the rotor displaces in its entirety in the axial direction. In this case, it is entirely possible that the rotor 10 displaces in the axial direction A in such a way that the distance of the lip 28 from the end face 107 becomes zero, or that the lip 28 even immerses into the central inlet area 25 of the rotor 10. Therefore, the feature that the lip 28 ends at a distance from the end face 107 refers to the state when the rotor 10 is in its desired position with respect to the axial direction A, so that the rotor 10 is centered with respect to the axial direction A with respect to the stator 100. In the drawing, the rotor 10 is always represented in this position centered with respect to the axial direction A.

The distance of the lip 28 from the end face 107 of the rotor 10 in the axial direction is referred to in the following as the lip distance DL. Thus, the lip distance DL refers to that operating state when the rotor 10 is centered with respect to the axial direction A.

The lip 28 serves as a tear-off edge for the fluid flowing into the pump chamber 23. Due to the lip 28, there is a well-defined location at which the tear-off of the fluid takes place. In this way, negative tear-off effects, which lead to cavitation and a reduction in efficiency, can at least be significantly reduced. It is understood that the lip 28, when viewed in the circumferential direction, does not have to be designed in a continuous manner, but can also be designed with interruptions.

Another effect of the lip 28 that projects into the pump chamber 23 is that the lip 28 significantly reduces the leakage flow that flows from the trailing edges 108 of the vanes in the direction of the inlet 21. The lip 28 reduces the free flow cross-section between the trailing edges 108 of the vanes and the inlet 21. Due to this reduction in the cross-section through which the leakage flow can flow, the leakage flow is also reduced, so that less fluid per unit of time flows back from the trailing edges 108 of the vanes 103 to the inlet. The reduction of the leakage flow increases the efficiency of the centrifugal pump 200 and thus also its energy efficiency.

In the first embodiment represented in FIG. 4, the lip 28 has a triangular profile, wherein the apex of the triangular profile faces the end face 107 of the rotor 10. The lip 28 has a depth T in the axial direction A, which indicates how far the lip 28 projects from the cover part 4 of the pump housing 2 into the pump chamber 23. The design of the lip 28 with the triangular profile is advantageous for the function of the lip 28 as a tear-off edge. Preferably, the lip 28 with the triangular profile is not designed in a sharp-edged manner, but the apex of the substantially triangular profile is designed with a finite and different from zero width in the radial direction.

The lip 28 has an outer diameter D2, which refers to the outer diameter D2 of the lip 28 at its axial end facing the rotor 10. In the first embodiment represented in FIG. 4, the outer diameter D2 of the lip 28 is smaller than the diameter D1 of the central inlet area 25 of the rotor 10. Therefore, the lip 28 can immerse into the central inlet area 25 if the rotor 10 is displaced upwards in the axial direction A in the operating state according to the representation.

As can be recognized in FIG. 4, the lip 28 is preferably designed in such a way that it widens in the flow direction. In particular in the first embodiment, the lip 28 is designed to widen conically, so that the interior space of the lip 28 is designed in the shape of a truncated cone.

Various variants for the first embodiment of the pump unit 1 are represented in FIGS. 5 to 8, wherein the representation corresponds in each case to that in FIG. 4. Thus, FIG. 5 to FIG. 8A are each sectional views, wherein the section is made along the axial direction A.

Figure 5:
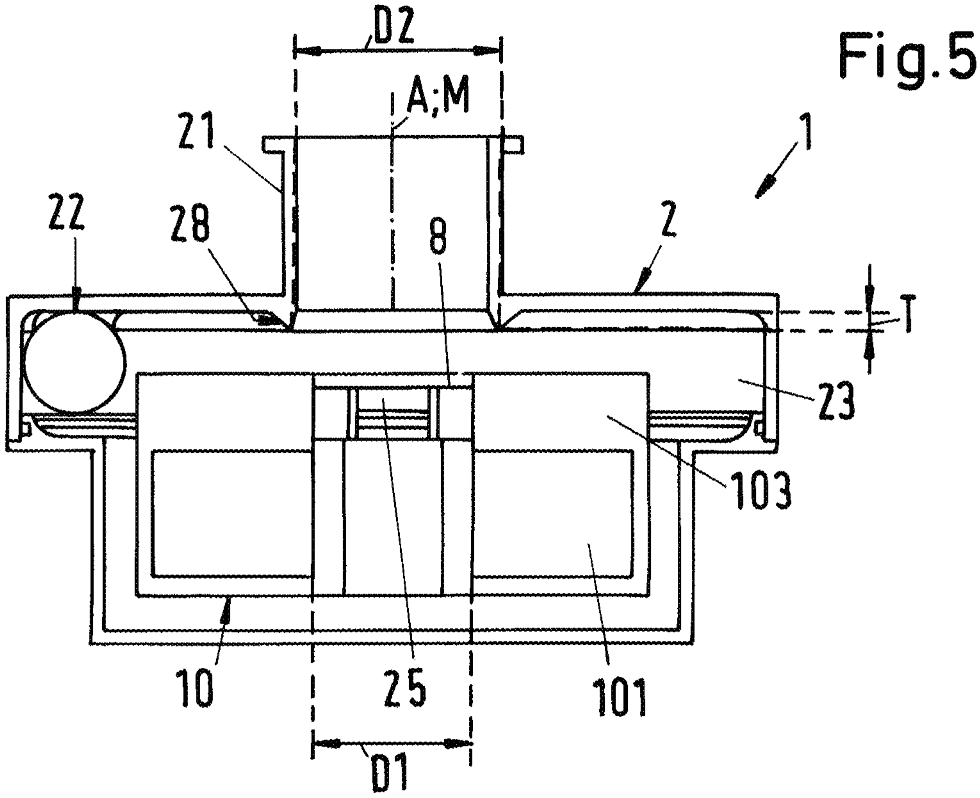
FIGS. 5-8B are different variants for the first embodiment, each in a view corresponding to that in FIG. 4.

In the variant represented in FIG. 5, the lip 28 has a lesser depth T, i.e. it projects less deeply into the pump chamber 23 with respect to the axial direction A. Furthermore, the outer diameter D2 of the lip 28 at its axial end facing the rotor 10 is greater than the diameter D1 of the central inlet area 25 of the rotor 10. Therefore, the lip 28 cannot immerse into the central inlet area 25.

Figure 6:
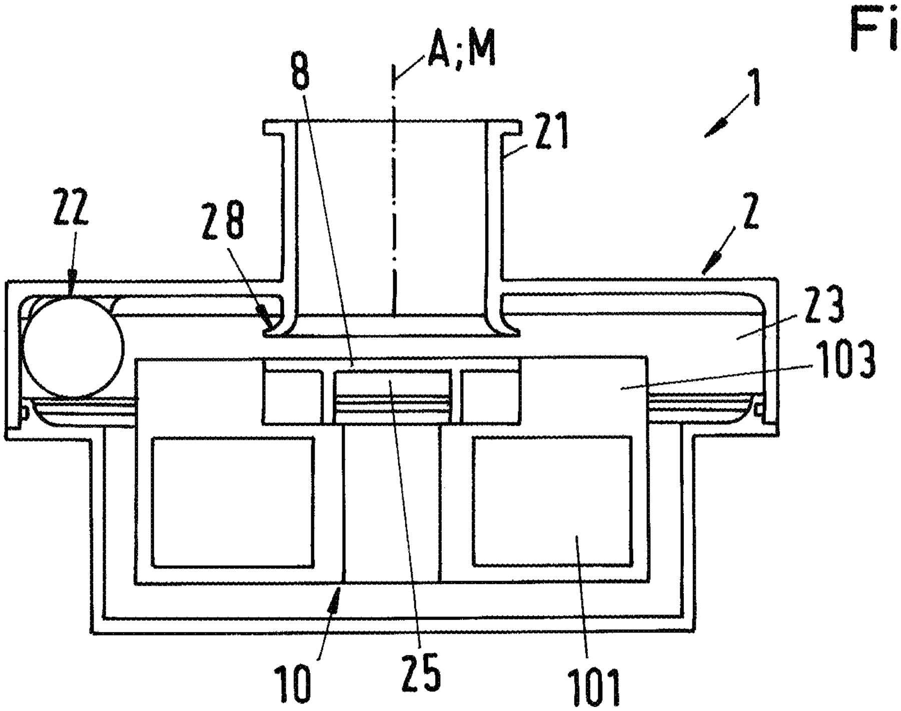

In the variant represented in FIG. 6, the lip 28 is curved outwards, so that the lip 28 widens again when viewed in the flow direction, but with a wall that is designed in a curved manner with respect to the axial direction A.

Figure 7:
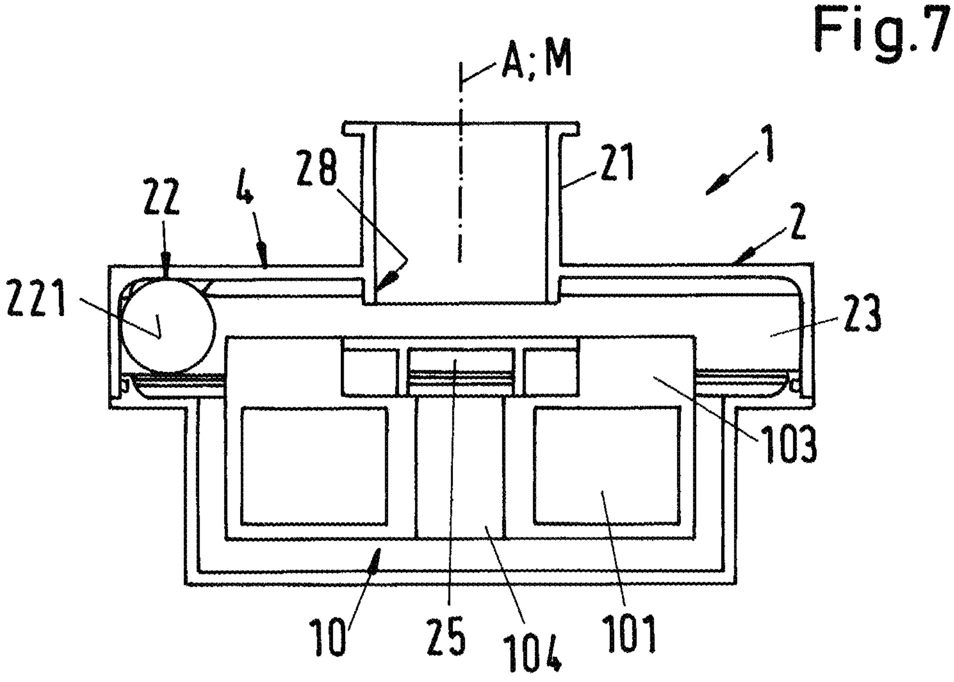

In the variant represented in FIG. 7, the lip 28 is designed as a cylindrical pipe section, i.e. with a constant inner diameter in the axial direction A. Here, it is possible—as represented in FIG. 7—that the lip 28 is designed in one piece with the cover part 4. In other embodiments, the lip 28 can also be designed as a separate component, for example as a hollow cylindrical pipe section which is attached in or at the inlet 21.

Figure 8A:
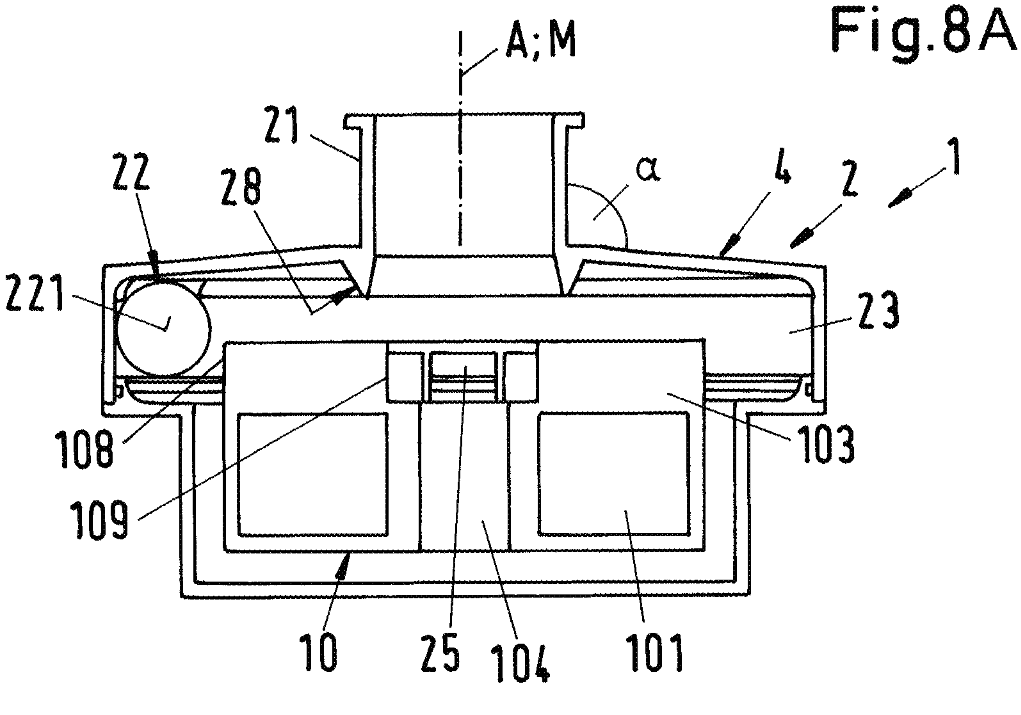

In the variant represented in FIG. 8A, the cover part 4 of the pump housing 2 is designed in an oblique manner so that the cover part 4 encloses an angle with the axial direction at the inlet 21 which is greater than 90°. The area of the cover part 4 adjacent to the inlet 21 is thus no longer parallel to the bottom of the pump housing 2 but rises towards the inlet 21.

Figure 8B:
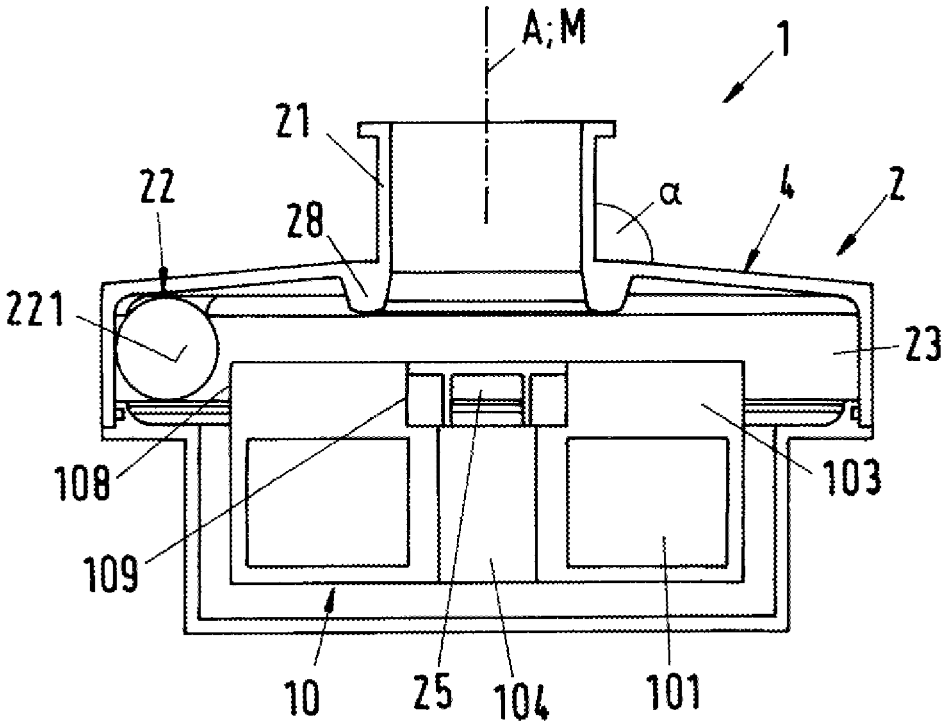

FIG. 8B shows a variant in which the end of the lip 28 facing the end face 107 of the rotor 10 is designed to be strongly flattened. This variant is particularly advantageous from a manufacturing point of view.

Figure 9:
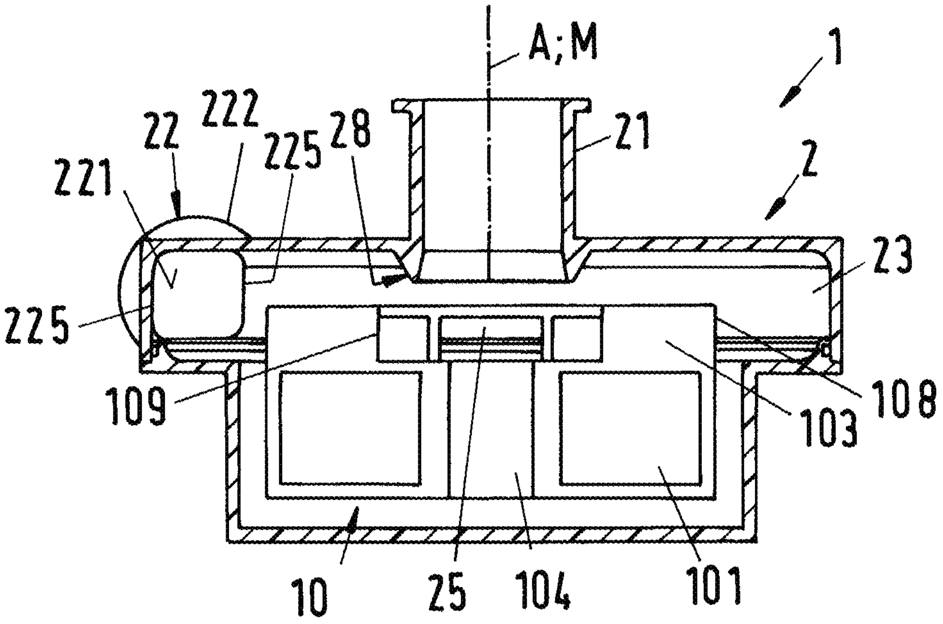
FIG. 9 is a second embodiment of a pump unit according to the disclosure in a sectional view along the axial direction.

FIG. 9 shows a second embodiment of a pump unit 1 according to the disclosure in a sectional view, wherein the section is made along the axial direction.

In the following, only the differences to the first embodiment will be discussed. The same parts or parts equivalent in function from the second embodiment are designated by the same reference signs as in the first embodiment. In particular, the reference signs have the same meaning as already explained in connection with the first embodiment. It is understood that all the preceding explanations of the first embodiment and its variants apply in the same way or analogously same way to the second embodiment.

The second embodiment differs from the first embodiment in the design of the entry surface 221 of the outlet 22, through which the fluid flows out of the pump chamber into the outlet 22.

While in the first embodiment (see for example FIG. 4) the profile of the entry surface 221 of the outlet 22 is designed as a circular surface, the second embodiment of the pump unit 1 according to the disclosure has an entry surface 221 of the outlet 22 which is different from a circular surface.

The outlet 22 further has an exit surface 222 (see also FIG. 2), through which the fluid leaves the outlet 22. As represented in FIG. 9, the profile of the exit surface 222 of the outlet 22 is a circular surface, in particular a circular surface that has a larger cross-sectional area than the profile of the entry surface. Thus, the outlet 22 is designed to widen when viewed in the flow direction and changes its cross-sectional area from the non-circular entry surface 221 to a circular exit surface.

In the embodiment represented in FIG. 9, the entry surface 221 of the outlet is designed such that it has several rectilinear edges 225. Here, the entry surface 221 is designed substantially in a rectangular manner and, in particular, substantially in a square manner. Furthermore, it is preferred if the profile of the entry surface 221 is designed with rounded corners, as represented in FIG. 9. Designing the entry surface 221 with a non-circular profile, for example with several edges 225, has the advantage that the cross-sectional area of the entry surface 221 can be made larger than with a circular profile, without having to enlarge the extension in the axial direction A, or that the entry surface 221 of the outlet 22 can be arranged closer to the vanes 103 or with a larger overlap with the vanes 103 with respect to the axial direction A.

In the following, the maximum extension of the profile of the entry surface 221 in the axial direction A is referred to as the profile height H1, and the maximum extension in the radial direction perpendicular to it as the profile width B1.

Furthermore, such embodiments of the profile of the entry surface 221 of the outlet 22 are also preferred in which the profile height H1 is smaller than the profile width B1. For example, the profile of the entry surface can be designed in a rectangular manner, wherein the profile width B1 is greater than the profile height H1. Due to this design, the center of the profile slips deeper compared to a circular profile of the same surface. In such an embodiment, the profile then has exactly four rectilinear edges 225, wherein the edges 225 that extend in the radial direction are longer than the edges 225 that extend in the axial direction A. The corners connecting two adjacent rectilinear edges 225 can be rounded, in the analogously same manner to that represented in FIG. 9 for the square profile of the entry surface 221.

In the following, two further variants for the profile of the entry surface 221 of the outlet 22 are explained on the basis of FIG. 10 and FIG. 11, in which the entry surface 221 has a profile which is different from a circular surface. In particular, designs are possible in which the profile is more rounded or even completely designed without rectilinear edges.

Figure 10:
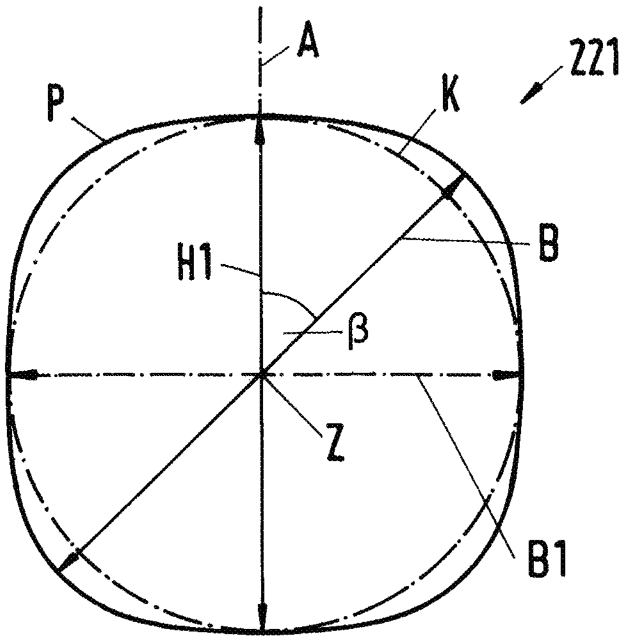
FIG. 10 is a first variant for the profile of the entry surface of the outlet.

In FIG. 10, a first variant for the profile of the entry surface 221 is represented. The profile is designated with the reference sign P. In this first variant, the profile height H1 is the same size as the profile width B1. Compared to the substantially square design of the profile represented in FIG. 9, for example, the profile P according to FIG. 10 is designed to be considerably more rounded.

For comparison, a circular surface K is also drawn in FIG. 10, whose diameter is the same size as the profile height H1 and the profile width B1. It can be clearly recognized that the cross-sectional area of the profile P is larger than the surface of the circle K.

Due to the profile P of the entry surface 221, which deviates from a circular surface, it is possible to design the profile P of the entry surface 221 of the outlet 22 with a larger cross-sectional area than in the circular design of the profile (see, for example, FIG. 4), without having to change the geometric dimensions of the pump housing 2. A larger cross-sectional area of the profile P of the entry surface 221 of the outlet 22 has the advantage that the pressure drop across the outlet 22, which is substantially determined by this cross-sectional area, can be reduced, which is advantageous with regard to the efficiency of the pump unit 1. Due to the reduced pressure drop across the outlet 22, the efficiency of the centrifugal pump 200 is increased.

Figure 11:
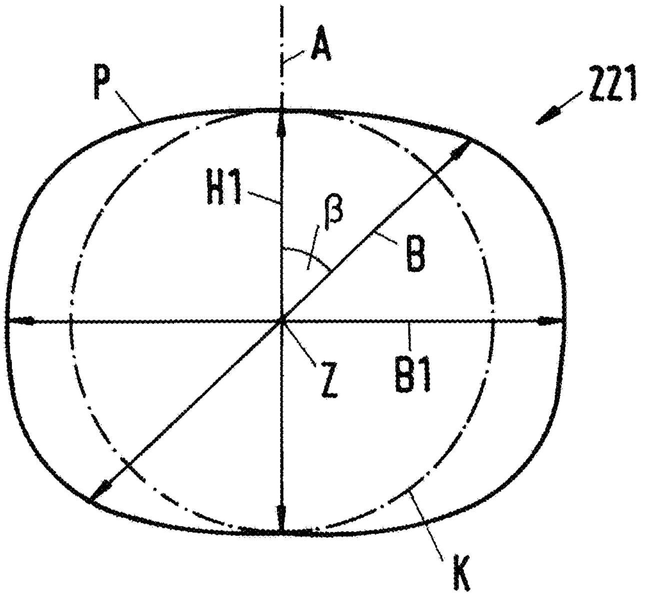
FIG. 11 is a second variant for the profile of the entry surface of the outlet.

In FIG. 11, a second variant for the profile P of the entry surface 221 is represented. In the second variant represented in FIG. 11, the profile width B1 is greater than the profile height H1. Due to this design of the profile P, the center Z of the profile P, or in the more general case of a non-symmetrical profile the center of gravity of the profile P, displaces with respect to the axial direction A downward according to the representation compared to a circular profile of the same cross-sectional area. In this design, in which the profile width B1 is greater than the profile height H1, the center Z or the center of gravity of the profile P is closer to the plane which divides the trailing edges 108 of the vanes 103 into two sections of equal height in the axial direction A.

Various designs of the profile P are possible, in which the profile width B1 is greater than the profile height H1. For example, a design as a strongly rounded rectangle is shown in FIG. 11. The rounding of the rectangle can be so strong that the profile no longer comprises any rectilinear edges in the strict sense. Furthermore, it is possible to design the profile in an elliptical manner. Usually, such designs are preferred in the second variant, in which there is at least a second direction B in which the profile P has a maximum extension which is greater than the profile height H1, i.e. the maximum extension of the profile in the axial direction A, wherein this second direction B encloses an angle β different from zero with the axial direction A. In the representation in FIG. 11, the second direction B includes the angle β=45° with the axial direction A by way of example.

Furthermore, the centrifugal pump 200 for conveying a fluid with a pump unit 1 is proposed by the disclosure, wherein the pump unit 1 is designed according to the disclosure. In a schematic sectional view, FIG. 12 shows an embodiment of a centrifugal pump 200 according to the disclosure. The centrifugal pump 200 comprises the stator 100, which extends in the axial direction A from a first axial end 110 to a second axial end 120, wherein a cup-shaped recess (not represented in FIG. 12) is provided at the first axial end 110, into which the cylindrical cup 31 of the pump unit 1 can be inserted. The stator 100 together with the rotor 10 forms an electromagnetic rotary drive for rotating the rotor 10 about the axial direction A, wherein the stator 100 is designed as a bearing and drive stator with which the rotor 10 can be driven magnetically without contact and can be magnetically levitated without contact with respect to the stator 100, wherein the rotor 10 is passively magnetically stabilized with respect to the axial direction A and is actively magnetically levitated in a radial plane E perpendicular to the axial direction A.

The stator 100 comprises a stator housing, which is not represented in FIG. 12 for reasons of a better overview. However, the stator 100 can, for example, be designed in the analogous way as the stator 100' with the stator housing 130' represented in FIG. 1, whereby the recess 121' is provided in the stator housing 130', into which the cylindrical cup 31 of the bottom part 3 of the pump housing 1 is inserted.

Particularly preferably, the electromagnetic rotary drive with the rotor 10 and the stator 100 is designed as a temple motor, wherein the stator 100 has a plurality of coil cores 125, each of which comprises a longitudinal leg 126 extending from a first end in axial direction A to a second end, as well as a transverse leg 127 which is arranged at the second end of the longitudinal leg 126 and in the radial plane E. The transverse leg 127 extends in the radial direction from the longitudinal leg 126 inwards towards the rotor 10.

All first ends of the longitudinal legs 126—i.e. the lower ends according to the representation—are connected to each other by a back iron 122 for conducting the magnetic flux.

The coil cores 125 are arranged around the rotor 10 with respect to the circumferential direction, so that the rotor 10 is arranged between the transverse legs 127 of the coil cores 125. At least one concentrated winding 160 is provided at each longitudinal leg 126, which winding surrounds the respective longitudinal leg 126.

The electromagnetic fields required for the magnetic drive and the magnetic levitation of the rotor 10 are generated with the concentrated windings 160. With these concentrated windings 160, those electromagnetic fields are thus generated in the operating state with which a torque is effected on the rotor 10 in a manner known per se, and with which an arbitrarily adjustable transverse force can be exerted on the rotor 10 in the radial direction, so that the radial position of the rotor 10, i.e. its position in the radial plane E perpendicular to the axial direction A, can be actively controlled or regulated. With respect to three further degrees of freedom, namely its position in the axial direction A and tilting with respect to the radial plane E perpendicular to the desired axis of rotation (two degrees of freedom), the rotor 10 is passively magnetically levitated or stabilized by reluctance forces, i.e. it cannot be controlled.

What is claimed is:

1. A pump unit for a centrifugal pump, which includes the pump unit and a stator extending in an axial direction from a first axial end to a second axial end, a cup-shaped recess disposed at the first axial end, into which the pump unit is capable of being inserted, the pump unit comprising:

a pump housing with an inlet and an outlet for a fluid to be conveyed; and a rotor arranged in the pump housing, the rotor including a plurality of vanes configured to convey the fluid, each vane of the plurality of vanes extending in the axial direction to an end face of the rotor facing the inlet, the pump housing delimiting a pump chamber, the rotor configured to be rotated about the axial direction, the pump unit configured for a non-contact magnetic levitation of the rotor and for a non-contact magnetic drive of the rotor by the stator, the pump housing having a cover part and a bottom part, the bottom part having a cylindrical cup to receive the rotor, the cup configured to be inserted into the cup-shaped recess of the stator, the inlet having a lip forming an axial end of the inlet, the lip projecting into the pump chamber and, when viewed in a flow direction, ends in front of the end face of the rotor when the rotor is centered with respect to the axial direction in an operating state, and the axial end forming the lip facing the rotor has a maximum depth closer to a central inlet area defined by an inlet diameter, in a radial direction, than to a trailing edge of the plurality of vanes of the rotor.

2. The pump unit according to claim 1, wherein the plurality of vanes of the rotor are arranged around the central inlet area which extends in the axial direction to the end face of the rotor and which includes the inlet diameter.

3. The pump unit according to claim 2, wherein the rotor has at least one relief opening extending from the central inlet area in the axial direction through the rotor.

4. The pump unit according to claim 2, wherein the lip of the inlet has an outer diameter which is larger than the inlet diameter of the central inlet area.

5. The pump unit according to claim 1, wherein the lip has a substantially triangular profile, an apex of the triangular profile facing the end face of the rotor.

6. The pump unit according to claim 1, wherein the lip widens when viewed in the flow direction.

7. The pump unit according to claim 1, wherein the lip is outwardly curved.

8. The pump unit according to claim 1, wherein the lip is a cylindrical pipe section.

9. The pump unit according to claim 1, wherein the cover part of the pump housing is oblique so that the cover part encloses an angle with the axial direction at the inlet which is greater than 90°.

10. The pump unit according to claim 1, wherein the outlet has an entry surface through which the fluid is capable of flowing from the pump chamber into the outlet, and the entry surface has a profile which is different from a circular surface.

11. The pump unit according to claim 10, wherein the profile of the entry surface is substantially rectangular.

12. The pump unit according to claim 10, wherein the profile of the entry surface has rounded corners.

13. The pump unit according to claim 10, wherein the profile of the entry surface has a profile height in the axial direction and a profile width in the radial direction perpendicular to the axial direction, and the profile width is greater than the profile height.

14. A centrifugal pump for conveying a fluid, comprising:

the pump unit according to claim 1; and the stator extending in the axial direction from the first axial end to the second axial end, the cup-shaped recess disposed at the first axial end, into which the cylindrical cup of the pump unit is capable of being inserted, the stator together with the rotor forming an electromagnetic rotary drive to rotate the rotor about the axial direction, the stator is a bearing and drive stator with which the rotor is capable of being magnetically driven without contact and capable of being magnetically levitated without contact with respect to the stator, the rotor passively magnetically stabilized with respect to the axial direction and actively magnetically levitated in a radial plane perpendicular to the axial direction.

15. The centrifugal pump according to claim 14, wherein the electromagnetic rotary drive is a temple motor, the stator has a plurality of coil cores, each of the coil cores of the plurality of coil cores comprising a longitudinal leg extending from a first end in the axial direction to a second end, and a transverse leg arranged at the second end of the longitudinal leg and in the radial plane and extending from the longitudinal leg in the radial direction, the plurality of coil cores arranged around the rotor with respect to a circumferential direction, so that the rotor is arranged between the transverse legs of the plurality coil cores, and at least one concentrated winding is disposed at and surrounds the longitudinal leg of each coil core of the plurality of coil cores.

16. The pump unit according to claim 1, wherein the lip has an outer diameter which is smaller than twice the inlet diameter of the central inlet area.

* * * * *